United States Patent
Mondon et al.

(10) Patent No.: US 11,382,853 B2
(45) Date of Patent: Jul. 12, 2022

(54) HYALURONIC ACID DERMAL FILLERS CROSSLINKED WITH CITRIC ACID, METHOD FOR MAKING SAME AND USES THEREOF

(71) Applicant: Anteis S.A., Plans-les-Ouates (CH)

(72) Inventors: Karine Mondon, Frangy (FR); Samuel Gavard Molliard, Bogeve (FR)

(73) Assignee: ANTEIS S.A., Plans-les-Ouates (CH)

( * ) Notice: Subject to any disclaimer, the term of this patent is extended or adjusted under 35 U.S.C. 154(b) by 0 days.

(21) Appl. No.: 16/348,611

(22) PCT Filed: Nov. 10, 2017

(86) PCT No.: PCT/EP2017/078843
§ 371 (c)(1),
(2) Date: May 9, 2019

(87) PCT Pub. No.: WO2018/087272
PCT Pub. Date: May 17, 2018

(65) Prior Publication Data
US 2019/0269597 A1    Sep. 5, 2019

(30) Foreign Application Priority Data

Nov. 11, 2016    (EP) .................... 16002392

(51) Int. Cl.
| | |
|---|---|
| *A61K 8/365* | (2006.01) |
| *A61K 8/73* | (2006.01) |
| *A61K 8/42* | (2006.01) |
| *A61Q 19/08* | (2006.01) |

(52) U.S. Cl.
CPC .............. *A61K 8/735* (2013.01); *A61K 8/365* (2013.01); *A61K 8/42* (2013.01); *A61Q 19/08* (2013.01); *A61K 2800/91* (2013.01)

(58) Field of Classification Search
None
See application file for complete search history.

(56) References Cited

U.S. PATENT DOCUMENTS

| | | | |
|---|---|---|---|
| 8,357,795 B2 * | 1/2013 | Lebreton | A61L 27/54 536/124 |
| 8,658,147 B2 * | 2/2014 | Sannino | C08J 3/24 424/78.01 |
| 2003/0032937 A1 * | 2/2003 | Griego | A61M 25/0026 604/508 |
| 2013/0096081 A1 | 4/2013 | Njikang et al. | |

FOREIGN PATENT DOCUMENTS

| | | |
|---|---|---|
| CN | 103041448 B | 9/2015 |
| EP | 1939219 A1 | 7/2008 |
| WO | 2013109959 A1 | 7/2013 |
| WO | 2016179269 A1 | 11/2016 |

OTHER PUBLICATIONS

Google translation of CN 103 041 448 (Sep. 2015) (Year: 2015).*
International Search Report for PCT/EP2017/078843, dated May 1, 2018.
Michael Song, "An Introduction to Prefilled Syringe Selection—Prefilled Syringes With Staked-In Needles," Pharmaceutical Online, (2019), 1-3.

* cited by examiner

*Primary Examiner* — Craig D Ricci
(74) *Attorney, Agent, or Firm* — McBee Moore & Vanik IP, LLC

(57) ABSTRACT

The present invention generally relates to hyaluronic acid-based compositions for aesthetic use, and more specifically to a dermal filler composition comprising hyaluronic acid crosslinked with citric acid or a salt thereof. Furthermore, the present invention relates to a method for preparing said dermal filler composition and its use for aesthetic purposes, in particular for skin rejuvenation and correction of fine lines.

13 Claims, No Drawings

HYALURONIC ACID DERMAL FILLERS CROSSLINKED WITH CITRIC ACID, METHOD FOR MAKING SAME AND USES THEREOF

CROSS-REFERENCE TO RELATED APPLICATIONS

This application is the National Stage entry of International Application No. PCT/EP2017/078843, filed 10 Nov. 2017, which claims priority to European Patent Application No. 16002392.5, filed 11 Nov. 2016

BACKGROUND

Field of the Invention

The present invention generally relates to hyaluronic acid-based compositions for aesthetic use, and more specifically to a dermal filler composition comprising hyaluronic acid crosslinked with citric acid or a salt thereof. Furthermore, the present invention relates to a method for preparing said dermal filler composition and its use for aesthetic purposes, in particular for skin rejuvenation and correction of fine lines.

Description of Related Art

Nonsurgical rejuvenation procedures using injectable dermal fillers are currently considered to be the second most common non-surgical aesthetic treatments performed worldwide, behind botulinum toxin injections. While there are numerous filler types available to the clinician, hyaluronic acid is by far the most commonly utilized filler material today.

Hyaluronic acid is a natural polysaccharide composed of linked repeating units of N-acetyl-D-glucosamine and D-glucuronic acid. It is found throughout the human body (e.g., in the skin) and is generally well tolerated and safe. Because of its ability to bind and hold water, hyaluronic acid also play a supportive role in skin hydration. Furthermore, hyaluronic acid exhibits excellent viscoelastic properties and has a high tissue-lifting capacity (volumizing effect), making hyaluronic acid the dermal filler material of choice.

Unfortunately, hyaluronic acid is rapidly degraded in vivo by enzymatic and free radical degradation, resulting in an in vivo half-life of only about 24-48 hours. Therefore, in most commercial products, hyaluronic acid is crosslinked to increase its longevity. While many different crosslinking agents have been investigated and used in crosslinked hyaluronic acid products, 1,4-butanediol diglycidyl ether (BDDE) is now the most commonly used crosslinking agent, ahead of other crosslinkers such as divinyl sulfone (DVS) and 2,7,8-diepoxyoctane (DEO).

Despite being the current industry standard, BDDE has some disadvantages. For example, any BDDE-crosslinked HA product always contains some amounts of unreacted (i.e. "free") BDDE as well as partially hydrolyzed BDDE (i.e. epoxydioles; EPD). These "epoxide impurities" contain reactive epoxide groups and are therefore generally considered toxic. Therefore, a laborious purification procedure needs to be set up to remove these impurities to the greatest possible extent.

OBJECT OF THE INVENTION

In view of the above, the object of the present invention is to find a crosslinker having an improved safety profile while at the same time providing desirable rheological properties to the final dermal filler product.

SUMMARY OF THE INVENTION

The above object is achieved by using citric acid, or a salt thereof, for crosslinking hyaluronic acid (HA). The citric acid-crosslinked HA-based product offers excellent rheological properties for its use in cosmetic (aesthetic) applications, such as for skin rejuvenation and in the treatment of fine lines. Furthermore, the use of citric acid as a crosslinker is considered safer than the conventionally used BDDE crosslinker since citric acid is an intermediate in the Krebs (or tricarboxylic acid) cycle and is formed and metabolized in large amounts every day in humans.

In a first aspect, the present invention provides a dermal filler composition comprising crosslinked hyaluronic acid (HA), wherein the hyaluronic acid is crosslinked with citric acid or a salt thereof.

The HA dermal filler composition is generally present in the form of an injectable crosslinked gel and has a range of properties well suited for its use as dermal filler. In particular, the crosslinked gel was found to be sufficiently stable to heat sterilization to provide a sterile HA dermal filler with sufficiently high elastic modulus, low injection force and good flow properties.

In a second aspect, the present invention provides a method for making a dermal filler composition according to the first aspect of the invention comprising the steps of:
  (a) providing an aqueous mixture comprising hyaluronic acid (HA) in the non-crosslinked state and citric acid or a salt thereof,
  (b) reacting the aqueous mixture so as to obtain a citric acid-crosslinked HA gel product,
  (c) purifying the citric acid-crosslinked HA gel product, and
  (d) sterilizing the citric acid-crosslinked HA gel product to obtain a dermal filler composition.

The step of purifying the citric acid-crosslinked HA gel product is preferably conducted by dialysis and the step of sterilizing is preferably conducted by heat sterilization such as autoclave sterilization. The purification step is typically preceded by a neutralizing step, and optionally a swelling step.

In a third aspect, the present invention provides a dermal filler composition obtainable by the method according to the present invention.

In a fourth aspect, the present invention relates to a kit comprising a dermal filler composition according to the first and/or third aspect of the invention, and optionally instructions for use.

In a fifth aspect, the present invention relates to the use of a dermal filler composition according to the present invention (i.e. according to the first and/or third aspect of the invention) for cosmetic applications. Preferred applications of the dermal filler compositions include the use in skin rejuvenation (e.g. use as a "skin booster") and in the treatment of lines and folds, especially fine lines. Exemplary cosmetic applications include, but are not limited to, cosmetic treatments of facial lines, facial wrinkles, glabellar lines, nasolabial folds, marionette lines, buccal commissures, peri-lip wrinkles, crow's feet, décolettage, neck wrinkles, hands, and upper arms.

In a sixth aspect, the present invention provides a method for replacing or filling of a biological tissue or increasing the volume of a biological tissue for cosmetic purposes, in particular for cosmetic treatments as those mentioned above in connection with the fifth aspect, comprising administering to a subject in need thereof an effective amount of the dermal filler composition according to the present invention.

Preferred embodiments of the present invention are set forth in the appended claims. Further embodiments and other objects, advantages and features of the present invention will become apparent from the following detailed description of the invention and the examples.

DETAILED DESCRIPTION OF A PREFERRED EMBODIMENT

The present invention is based on the surprising finding that the use of citric acid or a salt thereof as a safer alternative to the commonly used BDDE crosslinker enables the manufacturing of a crosslinked HA gel suitable for use as a dermal filler in a simple and convenient one-step crosslinking process. The crosslinked HA gel of the present invention exhibits unique and suitable properties for use as a dermal filler, such as a sufficiently high modulus of elasticity (G') in combination with a low injection force through fine needles, and good flow characteristics.

Furthermore, since citric acid is a well-known intermediate in the citric acid cycle of the human body and is metabolized without generating any remarkable side-effects, even in very high concentrations, citric acid is expected to have an improved safety profile compared to that of other crosslinking agents such as BDDE. What is more, citric acid is considered to be a "green" crosslinker and also has price advantages over other compounds commonly used to crosslink HA. For all these reasons, citric acid is considered to be a safer alternative to conventionally used crosslinkers (e.g. BDDE) which holds promising potential for the development of dermal fillers, in particular of new filler products indicated for skin rejuvenation and/or the reduction of fine lines.

In a first aspect, the present invention relates to a dermal filler composition comprising crosslinked hyaluronic acid, wherein the hyaluronic acid is crosslinked with citric acid or a salt thereof.

The use of citric acid as a crosslinker results in covalent crosslinks between separate HA molecules (intermolecular crosslinks) and/or covalent crosslinks within the same HA molecule (intramolecular crosslinks). The crosslinked product is generally in the form of a three-dimensional network or "gel" structure. The term "gel", as used herein, usually refers to a material having fluidity at room or body temperature between that of a liquid and solid. Since it is generally capable of absorbing water it may also be referred to as "hydrogel" herein.

The term "dermal filler" or "dermal filler composition", as used herein, is intended to refer to a material designed to add volume to, or replace or augment volume of, soft tissue areas of skin. Generally, the dermal filler described herein is injectable, i.e. can be dispensed from syringes or similar devices under normal conditions under normal pressure to the desired target site (e.g., into the dermis and hypodermis). It is normally sterile and in the form of a gel, in particular in the form of a cohesive gel.

The term "cohesive" or "cohesivity" within the meaning of the present invention is defined as the capacity of a material (e.g., of a hydrogel) not to dissociate because of the affinity of its molecules for each other. This is, cohesivity is important with regard to gel integrity. In the context of the present invention, cohesivity can be determined using the Gavard-Sundaram Cohesivity Scale (Sundaram et al., Plast. Reconstr. Surg. 136:678-686, 2015). Preferably, the dermal filler of the present invention has a cohesivity of 3, 4 or 5 on the five-point Gavard-Sundaram Cohesivity Scale.

Within the present invention, HA is crosslinked using citric acid or a salt thereof. While citric acid is a tricarboxylic acid ($C_6H_8O_7$) having the following structural formula:

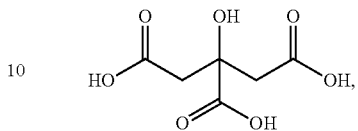

a "citric acid salt" within the meaning of the present invention generally relates to an alkali metal salt of citric acid, an alkaline earth metal salt of citric acid, a mixed alkali metal and alkaline earth metal salt of citric acid, or a combination thereof. Preferred citric acid salts for use herein include alkali metal salts of citric acid. Within the present invention, the alkali metal is preferably selected from sodium, potassium, or a combination thereof, and the alkaline earth metal is preferably selected from magnesium, calcium, or a combination thereof. Particularly suitable for use herein is sodium citrate (i.e. one or more of monosodium citrate, disodium citrate and trisodium citrate), potassium citrate (i.e. one or more of monopotassium citrate, dipotassium citrate and tripotassium citrate), or any combination thereof.

The term "hyaluronic acid" or "HA", as used herein, includes hyaluronic acid, hyaluronate, and any of its hyaluronate salts, such as salts of hyaluronate and sodium, potassium, lithium, magnesium, calcium, or combinations thereof. The term "non-crosslinked", as used herein, refers to HA molecules that are not crosslinked, or very lightly crosslinked (very low degree of crosslinking or essentially uncrosslinked, e.g., a degree of modification of less than 1% or less than 0.1%). The molecular mass of HA is not particularly limited and may be, for example, between $2.0 \times 10^5$ Da and $5.0 \times 10^6$ Da, preferably between $5.0 \times 10^5$ Da and $4.0 \times 10^6$ Da, more preferably between $1.0 \times 10^6$ Da and $3.5 \times 10^6$ Da, and most preferably between $2.0 \times 10^6$ Da and $3.0 \times 10^6$ Da.

It is further contemplated within the present invention that the HA of, or used for making, he dermal filler of the present invention is a mixture of two or more HA materials that differ from each other by their mean molecular weight. For example, the HA may comprise a mixture of high molecular weight HA having a molecular weight of, e.g., $2.0 \times 10^6$ Da to $4.0 \times 10^6$ Da, and a low molecular weight HA having a molecular weight of, e.g., $0.2 \times 10^6$ Da to $1.0 \times 10^6$ Da.

The ratio of the high molecular weight HA to the low molecular weight HA may be between 10:90 to 90:10, particularly from 51:49 to 90:10 or from 65:35 to 80:20. In one embodiment, 50% or more, 60% or more, 70% or more, 80% or more, 90% or more, or 100% of the HA is comprised of HA having a molecular weight greater than $1.0 \times 10^6$ Da, preferably at least $1.0 \times 10^6$ Da and more preferably $2.0 \times 10^6$ Da to $4.0 \times 10^6$ Da.

It is also within the scope of the present invention that the HA is not only mono-crosslinked, i.e. crosslinked in a single crosslinking reaction, but double-crosslinked or triple-crosslinked in similar terms to the procedures used for manufacturing the BDDE-crosslinked gels disclosed in, e.g., WO 2005/085329 (polydensified HA gels) and WO 2014/198406 A1 (triple-crosslinked HA gels). In a preferred embodiment, the HA is mono-crosslinked with citric acid or a salt thereof.

Reference to "molecular weight" or "molecular mass" of HA are, for the purpose of the present invention, to be understood as indicating the viscosity average molecular mass ($M_v$). The viscosity average molecular mass can be calculated by relating the measured intrinsic viscosity ($\eta$) to the average molecular weight ($M_v$) by the following Mark-Houwink equation: $[\eta]=K \times M_v^a$, wherein $[\eta]$=intrinsic viscosity in $m^3/kg$, Mv=molecular mass, $K=2.26 \times 10^{-5}$ $m^3/kg$, and a=0.796.

The intrinsic viscosity may be measured at 25° C. using a buffer solution of 0.15 M sodium chloride in 0.01 M phosphate buffer solution (pH 7.0) by means of a suspended level viscometer (Ubbelohde type viscometer) according to the procedure defined in European Pharmacopoeia 7.0 (see sodium hyaluronate monograph 01/2011:1472)

In accordance with the present invention, the crosslinked hyaluronic acid is present in the dermal filler composition in an amount of between 1 mg/ml and 50 mg/ml, preferably between 5 mg/ml to 40 mg/ml, more preferably between 10 mg/ml and 35 mg/ml, still more preferably between 15 mg/ml and 30 mg/ml, and most preferably between 20 mg/ml and 25 mg/ml.

The degree of modification (MoD) of the crosslinked HA in the dermal filler composition, expressed as the ratio of the sum of mono-, double- and triple-crosslinked citric acid crosslinkers to the sum of HA repeating disaccharide units, is preferably from 0.5% to 50%, from 1% to 20%, from 5% to 15%, or about 10%.

The degree of modification can be determined by those skilled in the art using NMR in accordance with methods known in the art (see Edsman et al., Dermatol. Surg. 2012, 38:1170-1179; Guarise et al., Carbohydrate Polymers 2012, 88:428-434; and Kenne et al., Carbohydrate Polymers 2013, 91:410-418). A skilled person will be able to identify the characteristic peaks of HA and of the citric acid crosslinker so as to determine the degree of modification.

The dermal filler composition of the present invention exhibits a desired "smooth" appearance as desired and is generally cohesive. After heat sterilization (e.g., after autoclaving at 121° C. for 10 min), the dermal filler composition has one or more of the following properties: (a) a modulus of elasticity ($G'_{1\ Hz}$) of at least 50 Pa, particularly 50 Pa to 200 Pa or 100 Pa to 150 Pa, (b) a loss tangent ($\tan \delta_{1\ Hz}$) of less than 1.00, particularly less than 0.90, 0.80, 0.70, 0.60 or 0.50, and an injection force of less than 10 N, particularly less than 5 N, as determined through a 27G½ needle at an extrusion rate of about 0.21 mm/sec using a 1.0 ml glass syringe.

Within the context of the present invention, the dermal filler composition may comprise additional polymers, compounds or additives. In this respect, it is emphasized that the term "comprise", as used herein, for example in the context of "a compound comprising . . . " or "a method comprising . . . ", is intended to encompass both the open-ended term "includes" and the closed-ended phrase "consisting of".

In particular, the dermal filler composition of the present invention may further comprise non-crosslinked HA, for example as a lubricant to improve the filler's rheological properties such as to lower its extrusion force. The molecular weight of the non-crosslinked HA is preferably between $3.0 \times 10^5$ Da and $4.0 \times 10^6$ Da, in particular between $1.0 \times 10^6$ Da and $3.0 \times 10^6$ Da.

The amount of non-crosslinked HA present in the dermal filler is not specifically limited but is typically less than 200 mg/g or less than 150 mg/g, more preferably less than 150 mg/g or less than 100 mg/g, and most preferably less than 50 mg/g or less than 20 mg/g, and typically at least 0.001 mg/g or at least 0.01 mg/g, preferably at least 0.1 mg/g or at least 1 mg/g, more preferably at least 2 mg/g or at least 5 mg/g, and most preferably at least 10 mg/g or at least 20 mg/g. Preferably, the amount of non-crosslinked HA present in the dermal filler is from 0.001 mg/g to 100 mg/g, in particular from 0.1 mg/g to 50 mg/g, and more particularly from 1 mg/g to 10 mg/g. Alternatively, the dermal filler composition of the present invention may also be free of any added non-crosslinked HA, i.e. being devoid or essentially devoid of any non-crosslinked HA.

The dermal filler of the present invention may also comprise at least one crosslinked and/or non-crosslinked polysaccharide other than HA. Non-limiting examples of such optional polysaccharides are cellulose and cellulose derivatives (e.g. carboxymethyl cellulose (CMC) or hydroxypropyl methylcellulose (HPMC) and glycosaminoglycans (GAG) such as heparosan, chondroitin sulfate, and dermatan sulfate). In one embodiment, the other polysaccharide is (non-crosslinked) carboxymethyl cellulose (CMC). These other polysaccharides, in crosslinked or non-crosslinked form, may be present in the dermal filler in an amount of 20 wt. % or less, 15 wt. % or less, 10 wt. % or less, 8 wt. % or less, 6 wt. % or less, 4 wt. % or less, 2 wt. % or less, 1 wt. % or less or 0.01 wt. % or less. The lower limit is not specifically limited and may be, e.g., 0.001 wt. %. In a preferred embodiment, no polysaccharide(s) other than HA is present in the dermal filler composition of the present invention.

Furthermore, the dermal filler composition may optionally comprise an anesthetic, particularly a local anesthetic. The anesthetic is added for reducing pain caused by injection of the dermal filler. Generally, the total amount of anesthetic agent(s) included in the dermal filler composition of the present invention is in the range of 0.01 wt. % to 5 wt. % and, in particular, in the range of 0.1 wt. % to 2 wt. %.

Suitable local anesthetics for use herein include, but are not limited to, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquin, dimethocaine, diperodon, dycyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, psuedococaine, pyrrocaine, ropivacaine, salicyl alcohol, tetracaine, tolycaine, trimecaine, zolamine, and salts thereof. Combinations of two or more of the mentioned anesthetic agents, for example a combination of lidocaine and other "caine"-anesthetic(s) like prilocaine, may also be used herein.

Preferably, the at least one anesthetic agent is lidocaine or a salt thereof, such as lidocaine hydrochloride (lidocaine HCl). The lidocaine concentration in the compositions described herein, in particular in the dermal filler composition, may be in the range of 0.05 wt. % to 5 wt. %, for example, from 0.1 wt. % to 2.0 wt. % or from 0.2% to 1.0 wt. %. Preferably, the lidocaine concentration is about 0.3 wt. %.

The dermal filler composition of the present invention may further comprise, but is not limited to, one or more compounds selected from the group consisting of antioxidants (e.g., ascorbic acid and derivatives thereof, tocopherols, carotenoids and derivatives thereof, retinol, glutathione, and ubiquinones), amino acids (e.g., proline, lysine, arginine, leucine, isoleucine, and methionine), metal salts (e.g., a zinc salt), hydroxyapatite particles (e.g., calcium hydroxyapatite particles, preferably having a mean diameter of less than about 200 μm, e.g., 10 μm to 80 μm), as well as polyols and vitamins.

Suitable polyols include, but are not limited to, glycerol, mannitol, sorbitol, propylene glycol, erythritol, xylitol, maltitol, and lactitol. Particularly suitable for use herein is mannitol and glycerol. Further, the polyol is preferably glycol, optionally in combination with one or more of the aforementioned polyol compounds, in particular mannitol. The polyol(s) may, for example, be included in the injectable dermal filler composition in a concentration of 0.1% to 25% volume/volume or 1% to 20% volume/volume or 2% to 15% volume/volume, particularly in a concentration of 5% to 10% volume/volume.

Examples of vitamins include, but are not limited to, vitamin C, vitamin E and vitamins of the B group, i.e. one or more of $B_1$, $B_2$, $B_3$, $B_5$, $B_6$, $B_7$, $B_9$ and $B_{12}$ vitamins. The concentration of vitamin C or of vitamin E is preferably from about 0.01 mg/ml to about 10.0 mg/ml, more preferably from about 0.1 mg/ml to about 5.0 mg/ml, and the total concentration of the vitamins of the B group is preferably from about 0.01 mg/ml to about 10.0 mg/ml, more preferably from about 0.1 mg/ml to about 5.0 mg/ml. The total concentration of vitamins is generally 15 mg/ml or less, 10 mg/ml or less or 5 mg/ml or less. The vitamins may be present to stimulate and maintain cellular metabolism and, thus, to promote collagen production. Particularly preferred for use herein is vitamin C, vitamin E and vitamin $B_6$.

In a second aspect, the present invention relates to a method for making a dermal filler composition of the present invention comprising the steps of:
(a) providing an aqueous mixture comprising hyaluronic acid (HA) in the non-crosslinked state and citric acid or a salt thereof,
(b) reacting the aqueous mixture so as to obtain a citric acid-crosslinked HA gel product,
(c) purifying the citric acid-crosslinked HA gel product, and
(d) sterilizing the citric acid-crosslinked HA gel product to obtain a dermal filler composition.

In step (a) the citric acid or a salt thereof may be provided, or added to the aqueous mixture, as citric acid or a citric acid salt as defined hereinabove. The aqueous mixture provided in step (a) and subjected to crosslinking may have a pH of 5 to 10, particularly 6 to 10, 7 to 10, or 7 to 9.

The aqueous mixture can be provided in any way and is not limited to a particular sequence of steps. For example, HA may be combined with an aqueous solution (e.g. water, phosphate buffer or phosphate buffered saline) to obtain an aqueous mixture of hydrated HA in the non-crosslinked state, followed by contacting the aqueous mixture with citric acid. Alternatively, dry HA may be combined with an aqueous solution of citric acid or a salt thereof.

Step (b) comprises reacting the aqueous mixture with citric acid or a salt thereof under conditions that result in a citric acid-crosslinked HA gel product. The term "citric acid-crosslinked HA", as used herein, means HA crosslinked with citric acid or a salt thereof. The concentration of HA during crosslinking is typically between 50 mg/ml and 150 mg/ml, particularly between 75 mg/ml and 125 mg/ml, more particularly about 100 mg/ml.

The degree of crosslinking ($D_{cross}$), expressed as the molar ratio of citric acid present in the aqueous mixture provided in step (a) and subjected to crosslinking in step (b) to repeating disaccharide units of HA present in the aqueous mixture provided in step (a) and subjected to crosslinking in step (b) is usually in the range of 0.1 to 20, more typically in the range of 1 to 15 or 2 to 10, in particular in the range of 3 to 5.

The crosslinking temperature ($T_{cross}$) in °C. and the crosslinking time ($t_{cross}$) in minutes may be selected such that the following equation is satisfied: $(T_{cross})^{2.7} \cdot t_{cross} = 5 \times 10^5$ to $3 \times 10^7$, preferably $7 \times 10^5$ to $2 \times 10^7$ and more preferably $1 \times 10^5$ to $1 \times 10^7$. In addition, or separately, the crosslinking temperature ($T_{cross}$) is generally at least 25° C., preferably at least 30° C. or at least 35° C., more preferably at least 40° C., at least 45° C. or at least 50° C.

The upper limit of the crosslinking temperature is determined by the tendency of HA gels to degrade at excessively high temperatures. Those skilled in the art will be readily able to select appropriate temperatures to limit degradation to an acceptable level. Although not intended to be limiting, the upper temperature limit may be, for example, 65° C., 60° C., 55° C. or 50° C. Thus, exemplary suitable temperature ranges are 25° C. to 65° C., 30° C. to 60° C., 35° C. to 55° C., 40° C. to 55° C., or 45° C. to 50° C.

After crosslinking, the reaction mixture obtained from step (b) is generally neutralized by adding an appropriate amount of an aqueous solution containing an acid or base. To this extent, a solution of NaOH or HCl in water, phosphate buffer or phosphate buffered saline may be used. However, the neutralizing step may also simultaneously occur with purification, such as in the course of dialysis.

Optionally, a swelling step may be carried out before purification (and after the neutralizing step, if present) in which the hydrated, crosslinked HA gels are allowed to swell in an aqueous solution (e.g. in a phosphate buffer, especially in a phosphate buffered saline) for a given time (e.g., 6 h to 50 h) and temperature (e.g., 2° C. to 8° C.). Alternatively, the swelling is not a separate step but may occur concurrently with the purification, such as during dialysis.

Step (c) of purifying the citric acid-crosslinked HA gel product may be accomplished by methods such as alcohol precipitation or dialysis. The purification step serves to remove undesired impurities, in particular unreacted citric acid crosslinker. Additional water or an aqueous buffer solution may be optionally added after purification (e.g., dialysis) to adjust the HA concentration of the gel as desired.

In the context of the present invention, the citric acid-crosslinked HA gel is preferably purified by dialysis. The dialysis is usually carried out at low temperatures, e.g., at a temperature of about 2° C. to 8° C. However, higher temperatures may also be used provided the degradation of HA is still within an acceptable level. Generally, the dialysis is carried out for 6 h to 96 h, typically for about 12 h to 50 h, with multiple buffer changes, and the volume of the dialysis buffer is commonly at least 50 to 200 times the volume of the gel sample. Other suitable conditions for dialysis will be readily apparent to those skilled in the art.

The dialysis buffer used for the dialysis is not particularly limited. For example, a phosphate buffer may be used, such as a phosphate buffered saline. A "phosphate buffered saline" within the meaning of the present invention is a phosphate buffer containing one or more salts such as sodium chloride, potassium chloride, calcium chloride, and magnesium chloride. The phosphate concentration may be from about 1.0 mM to about 100 mM, particularly from about 5 mM to about 50 mM or from about 10 mM to about 20 mM. The pH of the dialysis buffer may be from 6.0 to 8.0, preferably from 6.5 to 7.8, more preferably from 6.8 to 7.4. Furthermore, the dialysis buffer (e.g., a phosphate buffer) preferably contains sodium chloride in an amount so that the osmolality of the dialysis buffer is between about 250 mOsm/kg to 350 mOsm/kg.

It is also contemplated within the present invention that the method optionally comprises adding non-crosslinked HA and/or an anesthetic, particularly lidocaine, to the CA-crosslinked HA gel product before sterilization. Furthermore, the pH may be adjusted to a desired value either before or after the addition of an anesthetic like lidocaine. Moreover, the method usually comprises one or several homogenization steps, e.g., mechanical stirring step(s), sieving step(s), screening step(s) and the like, such as before or after dialysis and prior to sterilization.

In step (d), the citric acid-crosslinked crosslinked HA gel is sterilized to obtain a sterile dermal filler composition. This step is usually carried out by subjecting the crosslinked HA gel to sterilization by moist heat. Sterilization may be, for example, accomplished by autoclaving the gel under appropriate conditions, such as at a temperature of 121° C. to 130° C. for 1 to 20 minutes, e.g. at 121° C. for 5 minutes. Other suitable conditions are readily apparent to those skilled in the art.

Conveniently, the citric acid-crosslinked HA gel may be sterilized in a syringe. Prior to filling the gel into the syringe, the gel is usually homogenized. The resulting sterile prefilled syringes are convenient forms for intradermal administration by injection, especially in the ready-to-use version.

As explained above in connection with the dermal filler composition according to the first aspect of the invention, the dermal filler composition may optionally contain one or more additional polymers, compounds or additives, including non-crosslinked HA, crosslinked and/or non-crosslinked polysaccharides other than HA, local anesthetics such as lidocaine, antioxidants, amino acids, metal salts, hydroxyapatite particles, polyols, and vitamins.

These optional compounds may be added to the crosslinked HA gel at any appropriate process stage before final sterilization, but are preferably added after dialysis and before sterilization. The explanations and definitions given above with respect to these additional polymers, compounds or additives apply, mutatis mutandis, to the method of the present invention.

In a third aspect, the present invention relates to a dermal filler composition obtainable by the method according to the present invention. In particular, this dermal filler composition is a dermal filler preparation that has been sterilized by moist heat, as described herein above.

The conditions of moist heat sterilization are preferably selected such that the resulting dermal filler is sterile and its rheological properties are not unduly decreased due to the exposure to high temperatures. For example, the modulus of elasticity (G') after sterilization is preferably not decreased by more than 60%, 50% or 40%, and more preferably not decreased by more than 30% or 20%, compared to the G' value before sterilization.

In a fourth aspect, the present invention relates to a kit comprising a dermal filler composition according to the present invention, more specifically according to the first and/or third aspect of the invention, and optionally instructions for use.

The kit preferably comprises a syringe prefilled with the dermal filler composition of the present invention. The instructions for use preferably prescribe that the intended use of the kit is for cosmetic applications, in particular those described herein. The term "cosmetic" is interchangeably used herein with the term "aesthetic".

In a fifth aspect, the present invention relates to the use of a dermal filler composition according to the present invention for cosmetic applications, e.g., for improving the visual appearance, in particular of the face.

Exemplary cosmetic applications in accordance with the present invention include, but are not limited to, augmenting or filling of wrinkles and lines of the skin, in particular of facial lines and facial wrinkles (e.g., glabellar lines, nasolabial folds, chin folds, marionette lines, buccal commissures, peri-oral wrinkles, and crow's feet). Other exemplary cosmetic applications include treating the perioral region, infra-orbital region, décolettage, neck wrinkles, hands, and upper arms and/or improve skin hydration and skin texture.

In a sixth aspect, the present invention relates to a method for replacing or filling of a biological tissue or increasing the volume of a biological tissue for cosmetic purposes, in particular for cosmetic treatments of skin lines and wrinkles, comprising administering to a subject in need thereof an effective amount of the dermal filler composition according to the present invention.

The dermal filler composition of the present invention is generally administered by injection, more specifically by subcutaneous or intradermal injection, using techniques known in the art such as the serial puncture technique. In particular, the dermal filler composition may be injected into the dermis and/or the subcutis, preferably into the deep dermis and/or upper subcutis. The term "effective amount", as used herein, is generally intended to refer to the amount of the dermal filler composition sufficient to effect beneficial or desired cosmetic (aesthetic) results. A "subject" in the sense of the present invention is any individual or patient, usually a human, in need of a treatment of a particular condition.

The present invention will now be further illustrated by the following, non-limiting example.

EXAMPLES

The examples below demonstrate that citric acid or a salt thereof can crosslink hyaluronic acid (HA) and leads to beneficial rheological properties of the resulting crosslinked HA gel product.

Sodium hyaluronic acid (NaHA) with a molecular mass of $3.3 \times 10^6$ Da was used for making the gels, and the crosslinking agent was citric acid or a salt thereof (in the following "citric acid" or "CA"). The reaction conditions were as follows:

initial weight $NaHA_{dry}$=3 g
molar $CA:HA_{disac.\ unit}$ ratio=~4.45
$time_{crosslinking}$=3 h
$temperature_{crosslinking}$=50° C.
$[NaHA]_{crosslinking}$=~100 mg/ml
$[NaHA]_{final}$=20 mg/ml Rheological Measurements The rheological measurements were performed using an AR2000 rheometer (TA Instruments) with a flat geometry of 40 mm and an air gap of 1,000 μm. The elastic modulus (G'), the viscous modulus (G"), and the loss tangent (tan δ=G"/G') were determined by a frequency scan from 0.1 to 100 Hz. These rheological values are indicated at 1 Hz. All rheological measurements, including the measurement of viscosity ($\eta_0$), were performed at a constant temperature of 25° C.

Measurement of Extrusion Force

The extrusion force (EF) was determined through a 27G½ TSK needle at an extrusion rate of 12.5 mm/min using a standard 1.0 ml glass syringe (BD) by means of an Ametek LS1 compression tester.

Example 1

Preparation of Citric Acid-Crosslinked HA Gels

A 22% citric acid solution with pH 6.6 was prepared by placing 38.65 g of a 5 M NaOH solution and 11.11 g of citric acid in a 50 ml flask. The pH was checked and, if the pH was 6.6, distilled water was added q.s. 50 ml and, if not, the pH was appropriately adjusted using a 5 M NaOH solution or a 1 M HCl solution. In addition, a 22% citric acid solution with pH 8.0 was prepared in the same manner, except that 38.7 g of a 5 M NaOH solution was placed in a 50 ml flask. Furthermore, a 22% citric acid solution with pH 9.8 was prepared in the same manner, except that 46.7 g of a 5 M NaOH solution was placed in a 50 ml flask.

33 g of each of the 22% (w/v) citric acid (CA) solution with pH 6.6 or pH 8.0 or pH 9.6 were then added to 3.3 g dry NaHA fibers (Mw=3.3×10⁶ Da; molar ratio of CA:$HA_{disaccharide\ unit}$=~4.45). The NaHA fibers in the CA solution were subjected to a first static hydration for 15 min and thereafter homogenized by hand mixing using a spatula for 10 min. After a second static hydration of the NaHA fibers in the CA solution for 45 min, the resulting mixture was homogenized by hand mixing for 10 min and then allowed to crosslink for 3 h at 50° C.

Thereafter, the obtained crosslinked gel was neutralized to pH=6.8 by addition of about 132 g of deionized water (gel at pH 6.6), 132 g of an aqueous HCl solution (gel at pH 8.0), and 132 g of a different aqueous HCl solution (gel with pH 9.8), and left to swell for about 12 h at 2-8° C. in a turbula shaker. After homogenizing the crosslinked gel for 10 min by stirring, the gel was filled into dialysis membranes (regenerated cellulose; separation limit: molecular mass=60 kDa) and dialyzed for 24 h at 2-8° C. against a phosphate buffer solution (pH=7) with four exchanges of the buffer solution to purify the gel and eliminating free, unreacted CA from the gel. The HA concentration of the final gel was 20 mg/ml. For the stability studies, the crosslinked gels were stored at RT for 14 days.

The gel was then put into standard 1 ml BD glass syringes and sterilized for 10 min or 20 min at 121° C. The pH, osmolarity, ejection force and rheology (frequency sweep and viscosity) of the obtained crosslinked gels and of the crosslinked gels stored for 14 days were measured before and after sterilization.

Example 2

Properties of Citrate-Crosslinked HA Gels Before and After Sterilization

The pH, osmolarity, ejection force (EF) and rheology (frequency sweep and viscosity) of the gels prepared in Example 1 were measured before and after sterilization 1 (121° C., 10 min) and sterilization 2 (121° C., 20 min). The results are shown in TABLES 1 to 3.

As can be seen from TABLE 1 below, the values for EF, G', G", tan δ and $\eta_0$ before sterilization are all within the same range for the three gels A, B and C. Furthermore, the pH values of the three gels are all within the desired range.

TABLE 1

Results before sterilization

| | | | | Rheological results After passing through 27G½ TSK needle | | | |
| --- | --- | --- | --- | --- | --- | --- | --- |
| | | | | Frequency sweep | | | Flow |
| Sample | pH | Osmolarity (mOsm/kg) | EF (N) | $G'_{(1\ Hz)}$ (Pa) | $G''_{(1\ Hz)}$ (Pa) | $\tan\delta_{(1\ Hz)}$ | $\eta_0$ (Pa·s) |
| Gel A (pH = 6.6_CA solution) | 6.94 (T = 21.9° C.) | 359 | 3.2 | 157 | 75 | 0.480 | 283 |
| Gel B (pH = 8.0_CA solution) | 7.04 (T = 21.9° C.) | 364 | 3.3 | 165 | 79 | 0.479 | 276 |
| Gel C (pH = 9.8_CA solution) | 6.95 (T = 21.9° C.) | 359 | 3.2 | 168 | 81 | 0.482 | 281 |

As can be seen from TABLE 2 below, the pH is essentially stable upon sterilization 1 (10 min at 121° C.), with a pH increase of only about 0.02 units. The ejection force is not significantly different from the value obtained before sterilization. No difference is observed for the osmolarity before and after sterilization 1. G' decreases by about 35-40% upon sterilization. Consequently, tan δ after sterilization 1 is higher than before sterilization.

TABLE 2

Results after sterilization 1 (10 min at 121° C.)

| | | | | Rheological results After passing through 27G½ TSK needle | | | |
| --- | --- | --- | --- | --- | --- | --- | --- |
| | | | | Frequency sweep | | | Flow |
| Sample | pH | Osmolarity (mOsm/kg) | EF (N) | $G'_{(1\ Hz)}$ (Pa) | $G''_{(1\ Hz)}$ (Pa) | $\tan\delta_{(1\ Hz)}$ | $\eta_0$ (Pa·s) |
| Gel A (pH = 6.6_CA solution) | 6.94 (T = 21.9° C.) | 360 | 4.2 | 96 | 69 | 0.716 | 92 |
| Gel B (pH = 8.0_CA solution) | 7.06 (T = 22.1° C.) | 358 | 4.0 | 96 | 69 | 0.721 | 101 |
| Gel C (pH = 9.8_CA solution) | 6.97 (T = 21.9° C.) | 360 | 3.7 | 100 | 72 | 0.713 | 94 |

As can be seen from TABLE 3 below, the values for the pH and the osmolality after sterilization 2 (20 min at 121° C.) are essentially identical to the values measured after sterilization 1 (10 min at 121° C.). The ejection force values increase by about 40-50% compared to the values measured before sterilization 1. As a result of sterilization 2, G' decreases by about 57-60% as compared to a decrease in G' of about 35-40% observed for sterilization 1. As a consequence, also tan δ after sterilization 2 is higher than after sterilization 1.

TABLE 3

Results after sterilization 2 (20 min at 121° C.)

| | | | | Rheological results After passing through 27G½ TSK needle | | | |
| --- | --- | --- | --- | --- | --- | --- | --- |
| | | | | Frequency sweep | | | Flow |
| Sample | pH | Osmolarity (mOsm/kg) | EF (N) | $G'_{(1\ Hz)}$ (Pa) | $G''_{(1\ Hz)}$ (Pa) | $\tan\delta_{(1\ Hz)}$ | $\eta_0$ (Pa · s) |
| Gel A (pH = 6.6_CA solution) | 6.95 (T = 22.0° C.) | 356 | 5.2 | 68 | 61 | 0.897 | 49 |
| Gel B (pH = 8.0_CA solution) | 7.07 (T = 22.0° C.) | 364 | 6.7 | 67 | 66 | 0.985 | 48 |
| Gel C (pH = 9.8_CA solution) | 6.98 (T = 21.9° C.) | 357 | 3.7 | 69 | 62 | 0.899 | 51 |

In summary, the above results show that crosslinking of HA with CA is possible and leads to gels with interesting and valuable properties. Although the properties of the gels are significantly impaired by sterilization (which likely impacts the ester linkages formed by the CA crosslinking), especially upon sterilizing for a prolonged period of time (e.g. loss of G' of about 35-40% and about 57-60% after sterilizations 1 and 2, respectively), the properties of the final sterile gels (e.g., a low to medium G' of about 60-100 Pa) are very useful and promising with regard to the development of new HA filler products.

Example 3

Stability of CA-Crosslinked HA Gels Before and After Sterilization

The pH, osmolarity, ejection force and rheology (frequency sweep and viscosity) of the gels prepared in Example 1 and stored for 14 days after crosslinking were measured both before and after sterilization 1 (121° C., 10 min) and sterilization 2 (121° C., 20 min). The results are shown in TABLES 4 to 6.

As can be seen from TABLE 4 below, the values for pH, EF, G', G", tan δ and $\eta_0$ measured 14 days after crosslinking and before sterilization are highly similar (almost identical) to the respective values before sterilization shown in TABLE 1. Thus, these results show that the three tested gels show stable properties over time.

TABLE 4

Results 14 days after crosslinking - before sterilization

| | | | | Rheological results After passing through 27G½ TSK needle | | | |
| --- | --- | --- | --- | --- | --- | --- | --- |
| | | | | Frequency sweep | | | Flow |
| Sample | pH | Osmolarity (mOsm/kg) | EF (N) | $G'_{(1\ Hz)}$ (Pa) | $G''_{(1\ Hz)}$ (Pa) | $\tan\delta_{(1\ Hz)}$ | $\eta_0$ (Pa · s) |
| Gel A (pH = 6.6_CA solution) | 6.92 (T = 23.0° C.) | 360 | 3.1 | 160 | 77 | 0.481 | 299 |
| Gel B (pH = 8.0_CA solution) | 7.04 (T = 22.8° C.) | 367 | 3.3 | 163 | 78 | 0.479 | 302 |
| Gel C (pH = 9.8_CA solution) | 6.94 (T = 22.7° C.) | 374 | 3.2 | 167 | 79 | 0.473 | 297 |

As can be seen from TABLES 4 and 5 below, the values for pH, EF, G', G", tan δ and $\eta_0$ measured 14 days after crosslinking and after sterilization for 10 min at 121° C. (sterilization 1) or for 20 min at 121° C. (sterilization 2) are highly similar (almost identical) to the respective values after sterilizations 1 and 2 shown in TABLE 2 and TABLE 3, respectively. Hence, these results show remarkably stable properties over time for the three tested gels.

TABLE 5

Results 14 days after crosslinking - after sterilization 1 (10 min at 121° C.)

| | | | | Rheological results After passing through 27G½ TSK needle | | | |
| --- | --- | --- | --- | --- | --- | --- | --- |
| | | | | Frequency sweep | | | Flow |
| Sample | pH | Osmolarity (mOsm/kg) | EF (N) | $G'_{(1\ Hz)}$ (Pa) | $G''_{(1\ Hz)}$ (Pa) | $\tan\delta_{(1\ Hz)}$ | $\eta_0$ (Pa · s) |
| Gel A (pH = 6.6_CA solution) | 6.95 (T = 23.3° C.) | 359 | 3.5 | 95 | 68 | 0.716 | 94 |
| Gel B (pH = 8.0_CA solution) | 7.06 (T = 22.9° C.) | 362 | 3.6 | 96 | 70 | 0.729 | 92 |
| Gel C (pH = 9.8_CA solution) | 6.97 (T = 22.7° C.) | 361 | 3.7 | 96 | 70 | 0.729 | 103 |

TABLE 6

Results 14 days after crosslinking - after sterilization 2 (20 min at 121° C.)

| | | | | Rheological results After passing through 27G½ TSK needle | | | |
| --- | --- | --- | --- | --- | --- | --- | --- |
| | | | | Frequency sweep | | | Flow |
| Sample | pH | Osmolarity (mOsm/kg) | EF (N) | $G'_{(1\ Hz)}$ (Pa) | $G''_{(1\ Hz)}$ (Pa) | $\tan\delta_{(1\ Hz)}$ | $\eta_0$ (Pa · s) |
| Gel A (pH = 6.6_CA solution) | 6.97 (T = 22.5° C.) | 359 | 5.7 | 65 | 59 | 0.908 | 51 |
| Gel B (pH = 8.0_CA solution) | 7.08 (T = 22.0° C.) | 360 | 4.9 | 64 | 59 | 0.922 | 52 |
| Gel C (pH = 9.8_CA solution) | 6.99 (T = 22.5° C.) | 364 | 4.8 | 67 | 61 | 0.910 | 50 |

Overall, the experiments presented above show that the use of CA as a crosslinking agent results in CA-crosslinked HA gels with interesting and promising properties. In particular, it was observed that the use of CA as a crosslinking agent allows for the manufacturing of a "smooth" crosslinked HA gel after sterilization, with a low to medium G'. In view of the fact that CA is a well-known molecule that is present in the human body, CA is expected to have an improved safety profile and, thus, to represent a promising alternative crosslinker to BDDE which opens up the possibility to develop new filler products indicated for, e.g., skin rejuvenation and/or for the treatment of fine lines.

The invention claimed is:

1. A sterile injectable dermal filler composition comprising crosslinked hyaluronic acid, wherein the hyaluronic acid is covalently crosslinked with citric acid or a salt thereof and the dermal filler composition has a hydrogel structure,
    wherein after heat sterilization, the dermal filler composition has (c) an injection force of 6.7 N or less, as determined through a 27G½ needle at an extrusion rate of about 0.21 mm/sec using a 1.0 ml glass syringe, and optionally one or more of the following properties:
    (a) a modulus of elasticity ($G'_{1\ Hz}$) of 50 Pa to 200 Pa,
    (b) a loss tangent (tan $\delta_{1\ Hz}$) of less than 1.00.

2. The dermal filler composition of claim 1, wherein the citric acid salt is provided as an alkali metal salt, an alkaline earth metal salt, a mixed alkali metal and alkaline earth metal salt, or a combination thereof.

3. The dermal filler composition of claim 1, wherein the hyaluronic acid comprises hyaluronic acid having an average molecular weight greater than $1 \times 10^6$ Da.

4. The dermal filler composition of claim 1, wherein the hyaluronic acid is present in the dermal filler composition in an amount of between 1 mg/ml and 50 mg/ml.

5. The dermal filler composition of claim 1, wherein the degree of modification of the crosslinked HA, expressed as the ratio of the sum of mono-, double- and triple-linked citric acid crosslinkers to the sum of hyaluronic acid disaccharide units, is from 0.5% to 50%.

6. The dermal filler composition of claim 1, further comprising non-crosslinked HA and/or an anesthetic.

7. A kit comprising a dermal filler composition of claim 1, and optionally instructions for use.

8. A dermal filler composition according to claim 1 for cosmetic applications.

9. The dermal filler composition of claim 2, wherein the alkali metal is selected from sodium or potassium, and the alkaline earth metal is selected from magnesium or calcium.

10. The dermal filler composition of claim 6, wherein the anesthetic is lidocaine.

11. The dermal filler composition of claim 1, wherein the degree of modification of the crosslinked HA, expressed as the ratio of the sum of mono-, double- and triple-linked citric acid crosslinkers to the sum of hyaluronic acid disaccharide units, is from 5% to 15%.

12. The dermal filler composition of claim 1, wherein the hyaluronic acid is present in the dermal filler composition in an amount of between 20 mg/ml and 25 mg/ml.

13. The dermal filler composition of claim 1, wherein after heat sterilization, the dermal filler composition has (c) an injection force of less than 5 N, as determined through a 27G½ needle at an extrusion rate of about 0.21 mm/sec using a 1.0 ml glass syringe.

\* \* \* \* \*